United States Patent [19]

Liu

[11] Patent Number: 5,466,406
[45] Date of Patent: Nov. 14, 1995

[54] PROCESS OF TREATING FILAMENTS

[75] Inventor: Cheng-Kung Liu, Norwalk, Conn.

[73] Assignee: United States Surgical Corporation, Norwalk, Conn.

[21] Appl. No.: 254,982

[22] Filed: Jun. 7, 1994

Related U.S. Application Data

[62] Division of Ser. No. 989,069, Dec. 11, 1992, abandoned.

[51] Int. Cl.⁶ .......................... B29C 71/00; D01D 10/06; D06M 13/148
[52] U.S. Cl. .................... 264/103; 264/130; 264/211.14; 264/233
[58] Field of Search ................................. 264/103, 129, 264/130, 211.14, 233

[56] References Cited

U.S. PATENT DOCUMENTS

| | | |
|---|---|---|
| 1,219,451 | 3/1917 | Gardos . |
| 1,691,764 | 11/1928 | Kelly . |
| 2,151,952 | 3/1939 | Wasum . |
| 3,159,964 | 12/1964 | Kretsch . |
| 3,600,223 | 8/1971 | Glick et al. . |
| 3,671,542 | 6/1972 | Kwolek . |
| 3,819,587 | 6/1974 | Kwoleck . |
| 3,850,819 | 11/1974 | Shay . |
| 3,888,965 | 6/1975 | Kwolek . |
| 3,954,635 | 5/1976 | Cummings, Jr. et al. . |
| 3,954,721 | 5/1976 | Gross . |
| 3,963,432 | 6/1976 | Hauxwell et al. . |
| 3,984,600 | 10/1976 | Kawase et al. . |
| 4,047,533 | 9/1977 | Perciaccante et al. . |
| 4,052,500 | 10/1977 | Kreahling et al. . |
| 4,129,507 | 12/1978 | Marshall et al. . |
| 4,343,859 | 8/1982 | Lundberg et al. . |
| 4,371,485 | 2/1983 | Mathes et al. . |
| 4,388,926 | 6/1983 | Shalaby et al. . |
| 4,622,038 | 11/1986 | Login et al. . |
| 4,702,741 | 10/1987 | Dexheimer . |
| 4,748,267 | 5/1988 | Chang . |

OTHER PUBLICATIONS

Hawley's Condensed Chemical Dictionary, Van Nostrand Reinhold Company (New York), Eleventh Edition (1987), pp. 567–568.

*Primary Examiner*—Leo B. Tentoni

[57] ABSTRACT

A spin finish is applied to one or more as spun filaments. The spin finish, which can be a solution of glycerin in a solvent, can be easily removed from the filaments if desired by a water wash. Preferably, the spin finish is non-toxic and the filaments treated therewith are useful in forming surgical devices.

15 Claims, 1 Drawing Sheet

PROCESS OF TREATING FILAMENTS

This is a divisional of application Ser. No. 07/989,069, filed Dec. 11, 1992, now abandoned.

FIELD OF THE INVENTION

The present invention relates generally to spin finishes for fibers. More specifically, this invention relates to glycerol-containing compositions to be applied to fibers, methods of preparing such fibers, and surgical devices made from such fibers.

BACKGROUND OF THE INVENTION

Fiber finishing compositions are a necessary part of modern, high speed synthetic fiber manufacture. Virtually all operations performed on the fibers following their being spun from the melt require the presence of suitable fiber finishes to prevent snarling and breaking, thus enabling high fiber throughput. Generally speaking, a fiber finish must provide several qualities with respect to both the interaction between the fiber and the machinery on which it is processed, and also the interactions among the fiber filaments themselves. This property is usually termed "lubricity" although in reality the change in the interactions caused by the fiber lubricant may occasionally result in a desirable increase in friction as well as the decrease in friction ordinarily associated with the term "lubricant."

When producing fibers for use in surgical devices, a spin finish which remains on the device even in small amounts should be non-toxic. Alternatively, the spin finish must be vigorously washed from the fiber at some point during the preparation of the surgical device. Spin finishes containing vegetable oils, fatty acids and/or surfactants have been used in treating fibers employed in making surgical devices. Such finishes must normally be removed from the fibers by washing the fibers with solvents such as chlorofluorocarbons. However, the use of chlorofluorocarbons has recently raised environmental concerns. In addition, such washing requirements greatly increase the cost of fiber production.

Fiber treating compositions which contain glycerol or glycerol-related substances are described in British Patent No. 1,248,513 and in U.S. Pat. Nos. 1,219,415; 1,691,764; 2,151,952; 3,159,964; 3,954,721; 3,963,432; 4,124,543; 4,624,793; and 4,800,117.

U.S. Pat. No. 3,954,635 describes a xylene based fiber finish for absorbable glycolic acid polymer fibers.

U.S. Pat. No. 4,388,926 describes passing fibers used to make sutures through two heated glycerine baths during the drawing process.

U.S. Pat. No. 4,343,859 describes drawing fibers through a heated glycerine stretch bath.

SUMMARY OF THE INVENTION

It has now been found that fibers useful in making surgical devices can be treated with a finishing material which provides satisfactory lubricity, but which does not require removal by chlorofluorocarbon solvents. Applicant has discovered that glycerol-based spin finish compositions not only facilitate processing of the fibers, but also allows removal of the finish, if desired, but a simple water wash. The spin finish of this invention may be non-toxic, thereby eliminating the need for its vigorous removal from the fiber before the fiber is used for medical purposes.

DESCRIPTION OF PREFERRED EMBODIMENTS

Figure 1:
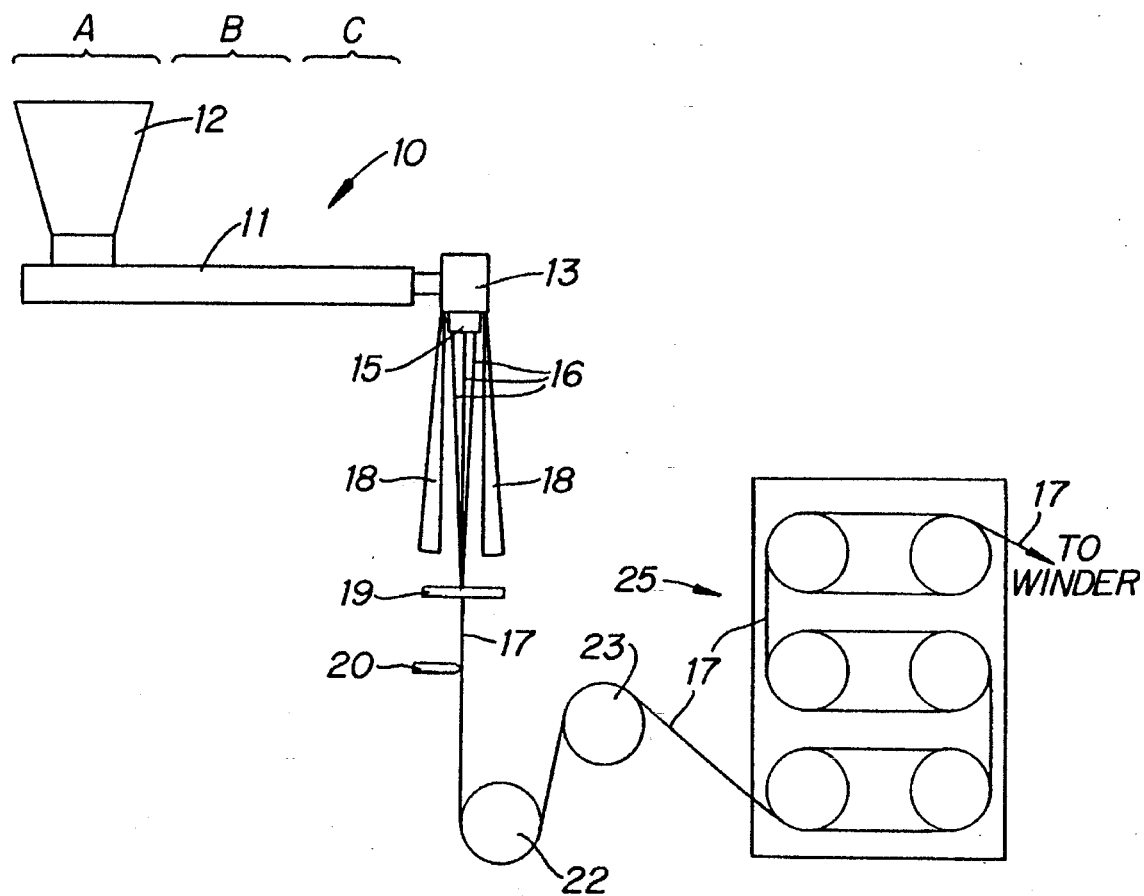
FIG. 1 is a schematic illustration of apparatus which is suitable for carrying out a preferred fiber manufacturing process in accordance with the present invention.

Glycerol-based spin finishes in accordance with the present invention contain glycerine dissolved in a suitable solvent to form a solution. The solution may contain glycerine in an amount from about 5 to about 45 percent by weight. Preferably, the spin finish solution contains from about 10 to about 25 percent by weight glycerine.

Suitable solvents for forming the spin finish are those which can form solutions containing up to 30 percent by weight glycerine. The solvent should be sufficiently volatile as to evaporate from the fiber to which the spin finish is applied, thereby leaving the glycerine on the fiber. The solvent should be one which has essentially no adverse affect on the fiber over the period of time from the application of the spin finish until the time the solvent evaporates. In particularly useful embodiments, where the fiber is used in a surgical device, the solvent is of a type which will have no adverse effect on humans in the event a small amount of the solvent remains on the fiber. This is particularly important when the surgical device is intended for implantation.

Suitable solvents include water, methanol, ethanol, n-propanol, isopropyl alcohol, n-butanol, sec-butanol, iso-butanol, and n-pentanol. Isopropyl alcohol is a particularly preferred solvent.

Due to the hygroscopic nature of glycerine, the spin finish will also likely include a certain amount of water. The amount of water in the spin finish will depend in large part on the environmental conditions in the area of preparation and application of the spin finish. Generally speaking, the amount of water present in the spin finish is not critical. Where the fiber being treated with the spin finish is subject to hydrolytic attack, it may be desirable to take steps to dry the fibers after application of the spin finish.

The spin finish may optionally include small amounts of other functional ingredients. For example, a fungicide or anti-bacterial agent such as hydroxy methylamino-alcohol and iodopropynyl butyl carbamate may be added to the spin finish. As another example, alkyl ammonium salt may be added to the spin finish as an antistatic agent. Other functional ingredients include butyl stearate, tridecyl stearate, oleic acid, glycerol monostearate, and trimethylolpropane tripelargonate. Normally, each optional functional ingredient will be present in an amount less than 1 percent by weight, and preferably less than 0.1 percent by weight.

The spin finish of this invention can be applied to yarns of any composition. The present spin finish is particularly useful for fibers made from those materials conventionally used in producing both absorbable and non-absorbable surgical devices. These materials include non-absorbable synthetic polymer such as polyamides, polyetheresters, polyesters, polyethylene terephthalate, polybutylene terephthalate, polypropylene, polyethylene, polystyrene, polycarbonate, polyetherimide ester, polyaryletherketone, polyether sulfone and synthetic absorbable polymers including those derived from glycolic acid, lactic acid, dioxanone, caprolactone, hydroxy butyric acid, valerolactone, trimethylene carbonate, as well as copolymers and blends thereof.

Known and conventional melt spinning apparatus can be used for the production of the multifilament yarns to be treated in accordance with this invention.

FIG. 1 schematically illustrates a filament manufacturing operation in accordance with the invention. Extruder unit 10 is of a known or conventional type and is equipped with controls for regulating the temperature of barrel 11 in various zones thereof, e.g., progressively higher temperatures in three consecutive zones A, B and C along the length of the barrel. Pellets or powder of resin to be spun into filaments are introduced to the extruder through hopper 12. Any of the polymeric resins which are useful for the formation of fibers can be used herein.

Motor-driven metering pump 13 delivers extruded resin at a constant rate through spinneret 15 possessing one or more orifices of desired diameter to provide a plurality of molten filaments 16. While spinneret 15 is shown schematically in FIG. 1 as extruding three filaments, it should be understood that the spinneret may extrude anywhere from 1 to 200 filaments simultaneously.

The filaments 16 travel downward and are gathered together by guide 19 to produce a yarn 17. The distance the filaments 16 travel after emerging from spinneret 15 to the point where they contact guide 19, i.e., the air gap, can vary and can advantageously be from about 0.5 m to about 10 m and preferably from about 1 m to about 2 m. A chimney 18, or shield, can be provided to isolate filaments 16 from contact by air currents which might otherwise affect the cooling or movement of the filaments in some unpredictable manner. In general, the temperature of zones A, B and C of the barrel 11 will vary depending on a number of factors such as the chemical nature of the resin, the size of the powder or pellets and the rate of feed. For polypropylene, for example, barrel zone A of the extruder can be maintained at a temperature of from about 215° to 250° C., zone B at from about 220° to 270° C. and zone C at from about 230° to about 270° C. Additional temperature parameters for spinning polypropylene include: the metering pump block may be maintained at from about 220° to about 250° C., the spin pack at from about 220° to about 250° C., and spinneret 15 may be maintained at from about 220° to about 250° C.

Once filaments 16 are gathered together by guide 19 to produce yarn 17, the spin finish is applied to yarn 17. The spin finish is thus applied to "as spun" filaments (i.e., to filaments which have not been drawn or otherwise treated, physically or chemically) which have been gathered into a yarn 17.

The spin finish can be applied using any known technique. As seen in FIG. 1, the yarn 17 may be passed along the edge of applicator 20 to which the spin finished is supplied at a predetermined rate. The spin finish should be supplied to the applicator at a rate which will cause the spin finish to be applied to the yarn at a rate of about 0.01 to about 5 mg per meter. Preferably the spin finish is applied to the yarn at a rate of about 0.04 to about 2 mg per meter.

The spin finish may be heated to a temperature between about 25° and 50° C. prior to application to the yarn to ensure rapid evaporation of the solvent. Alternatively, the environment around the applicator may be heated to a temperature between about 25° and 40° C. to ensure rapid volatilization of tile solvent. Preferably, however, a solvent is used which is sufficiently volatile to flash off without the need for external heating, other than that provided by the spinning operation.

The treated yarn can be processed in any manner after the application of the spin finish. The spin finish will assist in holding the individual filaments together, thereby preventing entanglement or separation of the filaments during subsequent processing. The spin finish also provides lubrication between the yarn and any rollers or godets employed in subsequent processing. In addition, the spin finish will function as a heat transfer medium during subsequent processing, such as drawing, to provide more uniform heating of the yarn than can be achieved by simply passing the yarn through heated air.

An example of subsequent processing is shown in FIG. 1. After application of the spin finish, the yarn may be wrapped around a lub godet 22 and one or more additional godets, for example, godet 23, to take up and adjust the tension on the yarn. The yarn 17 may then be passed to a heated draw frame 25. Draw frame 25 may be of any configuration. As shown in FIG. 1, draw frame 25 includes three pairs of godets which can be used to stretch the yarn or to allow relaxation and perhaps shrinkage of yarn 17. The speed at which the godets rotate and the temperature at which the draw frame is maintained will determine the amount of stretching and/or relaxation which occurs. Setting the various speeds and temperatures to achieve a desired result is within the purview of those skilled in the art.

Table I provides ranges of values for spinning and stretching parameters suitable for producing two types of yarns (polypropylene and copolymer of glycolide and lactide) which may be treated with a glycerol-based spin finish in accordance with the present invention.

TABLE I

| MELT SPINNING APPARATUS AND OPERATING CONDITIONS | | |
|---|---|---|
| Apparatus Component, Operating Parameter | For Polypropylene | Copolymer of Glycolide and Lactide |
| Extruder barrel temp., zone A, °C. | 215–250 | 210–240 |
| Extruder barrel temp., zone B, °C. | 220–270 | 220–250 |
| Extruder barrel temp., zone C, °C. | 230–270 | 220–250 |
| Extruder barrel pressure, psi | 1000–2000 | 700–1500 |
| Extruder barrel melt temp., °C. | 230–275 | 220–260 |
| Pump size, cc per rev. | .16–.584 | .16–.584 |
| Pump rpm | 25–35 for size .16 pump 6–10 for size .584 pump | 10–40 for size .16 pump 3–11 size .584 pump |
| Pump temp., °C. | 220–250 | 210–250 |
| Pump pressure, psi | 400–1000 | 500–1500 |
| Pump melt temp., °C. | 215–255 | 220–250 |
| Block temp., °C. | 220–250 | 220–250 |
| Clamp temp., °C. | 220–250 | 220–250 |

TABLE I-continued

MELT SPINNING APPARATUS AND OPERATING CONDITIONS

| Apparatus Component, Operating Parameter | For Polypropylene | Copolymer of Glycolide and Lactide |
|---|---|---|
| Adapter temp., °C. | 220–250 | 220–250 |
| Candle filter, screen, microns | 10–100 | 10–60 |
| No. of spinneret orifices | 10–200 | 5–200 |
| Diameter of spinneret orifices, .001 in | 5–30 | 5–30 |
| Spinneret temp., °C. | 220–250 | 210–250 |
| Spinneret pressure, psi | 400–1500 | 500–1500 |
| Spinneret melt temp., °C. | 220–250 | 215–250 |
| cc/hr output, per spinneret orifice | 5–20 | 5–20 |
| First pair of godets, °C. | 40–90 | 50–80 |
| First pair of godets, mpm | 100–300 | 80–200 |
| Second pair of godets, °C. | 70–130 | 60–120 |
| Second pair of godets, mpm | 300–1000 | 300–1200 |
| Draw (stretch) ratio | 2–8 | 2–6 |
| Third pair of godets, °C. | ambient | ambient |
| Third pair of godets, mpm | 250–1000 | 250–1150 |
| Shrinkage (relaxation), percent | 5–15 | 5–10 |

After drawing, the yarn may then be sent to a winder where it can be placed onto spools for storage while awaiting further treatment or use. The spin finish can be easily removed from the yarn by washing, for example, with water. The ease and low cost of spin finish removal is an advantage of the spin finish of the present invention. In addition, since the spin finish may be formulated entirely from ingredients which have been previously approved for surgical devices, stringent removal is not required for use of the yarn in a surgical device, such as an implantable surgical device.

The yarn may be formed into a surgical device using any known technique such as braiding, knitting, weaving, air-entangling, twisting, tying, winding, or forming a composite using the yarn or pieces thereof as a reinforcing component.

We claim:

1. A method of treating filaments comprising:
   spinning one or more filaments; and
   applying to said one or more filaments a spin finish comprising a compound of the formula $HOCH_2CH(OH)CH_2OH$, said applying step being performed on said one or more filaments as spun.

2. A method as in claim 1 wherein a plurality of filaments are spun in said spinning step and further comprising the step of gathering said plurality of filaments together to form a yarn prior to said applying step.

3. A method of treating filaments comprising: spinning one or more filaments; and applying to said one or more filaments a spin finish consisting essentially of glycerin and a solvent, said applying step being performed on said one or more filaments as spun.

4. A method as in claim 1 further comprising the step of forming a spin finish by dissolving said compound in a solvent to form a solution.

5. A method as in claim 4 wherein said spin finish comprises said compound in an amount from about 5 to about 45 percent by weight of the solution.

6. A method as in claim 4 wherein said spin finish comprises said compound in an amount from about 10 to about 25 percent by weight of the solution.

7. A method of producing a surgical device comprising:
   spinning one or more filaments;
   applying to said one or more filaments a spin finish comprising a compound of the formula $HOCH_2CH(OH)CH_2OH$, said applying step being performed on said one or more filaments as spun; and
   forming a surgical device made totally or in part from said filaments.

8. A method as in claim 7 wherein a plurality of filaments are produced in said spinning step and further comprising the step of gathering said plurality of filaments together to form a yarn prior to said applying step.

9. A method of producing a surgical device comprising:
   spinning one or more filaments;
   applying to said one or more filaments a spin finish consisting essentially of glycerine and a solvent, said applying step being performed on said one or more filaments as spun; and
   forming a surgical device made totally or in part from said filaments.

10. A method as in claim 7 further comprising the step of forming a spin finish by dissolving said compound in a solvent to form a solution.

11. A method as in claim 10 wherein said spin finish comprises said compound in an amount from about 5 to about 45 percent by weight of the solution.

12. A method as in claim 10 wherein said spin finish comprises said compound in an amount from about 10 to about 25 percent by weight of the solution.

13. A method as in claim 7 wherein said spin finish is non-toxic.

14. A method as in claim 7 further comprising the step of washing said one or more filaments to remove substantially all of the spin finish therefrom.

15. A method as in claim 14 wherein said washing step comprises exposing said one or more filaments to water.

* * * * *